United States Patent [19]
Kitazawa et al.

[11] Patent Number: 6,136,852
[45] Date of Patent: Oct. 24, 2000

[54] 3,4-DISUBSTITUTED PHENYLETHANOLAMINOTETRALIN-CARBOXYLIC ACID DERIVATIVES

[75] Inventors: Makio Kitazawa; Kosuke Okazaki; Tetsuro Tamai; Masaru Saito; Nobuyuki Tanaka; Hiroaki Kobayashi; Ken Kikuchi; Hideyuki Muranaka, all of Nagano, Japan

[73] Assignee: Kissei Pharmaceutical Co., Ltd., Nagano, Japan

[21] Appl. No.: 09/155,345

[22] PCT Filed: Mar. 26, 1997

[86] PCT No.: PCT/JP97/01008

§ 371 Date: Mar. 8, 1999

§ 102(e) Date: Mar. 8, 1999

[87] PCT Pub. No.: WO97/35835

PCT Pub. Date: Oct. 2, 1997

[30] Foreign Application Priority Data

Mar. 27, 1996 [JP] Japan .................................. 8-111077

[51] Int. Cl.[7] ........................ A61K 31/215; A61K 31/19; C07C 69/76; C07C 62/06
[52] U.S. Cl. ......................... 514/510; 514/532; 514/543; 514/569; 514/570; 514/571; 560/56; 560/60; 560/61; 560/75; 562/466; 562/470; 562/471; 562/478
[58] Field of Search ..................... 514/510, 532, 514/543, 569, 570, 571; 560/56, 60, 61, 75; 562/466, 470, 471, 478

[56] References Cited

FOREIGN PATENT DOCUMENTS 6-506676  7/1994  Japan .
92/18461  10/1992  WIPO .

*Primary Examiner*—Johann Richter
*Assistant Examiner*—Rosalynd Keys
*Attorney, Agent, or Firm*—Sughrue, Mion, Zinn, Macpeak & Seas, PLLC

[57] ABSTRACT

The present invention relates to 3,4-disubstituted phenylethanolaminotetralincarboxylic acid derivatives represented by the general formula:

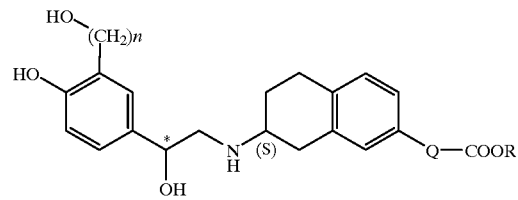

[wherein Q represents a vinylene group or a group represented by the general formula:

-A-$(CH_2)_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration] and pharmaceutically acceptable salts thereof, which have a selective $\beta_2$-adrenergic receptor stimulating effect with relieved burdens on the heart such as tachycardia and are useful as an agent for the prevention of threatened abortion and premature labor, a bronchodilator and an agent for pain remission and promoting stone removal in urolithiasis.

8 Claims, No Drawings

3,4-DISUBSTITUTED PHENYLETHANOLAMINOTETRALIN-CARBOXYLIC ACID DERIVATIVES

TECHNICAL FIELD

The present invention relates to novel 3,4-disubstituted phenylethanolaminotetralincarboxylic acid derivatives which are useful as medicaments.

More particularly, the present invention relates to 3,4-disubstituted phenylethanolaminotetralincarboxylic acid derivatives represented by the general formula:

(I)

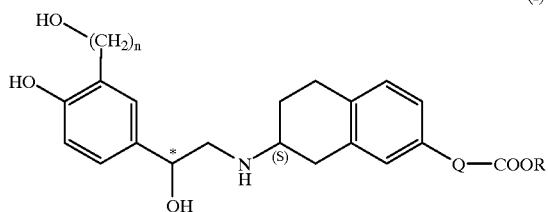

[wherein Q represents a vinylene group or a group represented by the general formula:

-A-(CH$_2$)$_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration] and pharmaceutically acceptable salts thereof, which have a selective $\beta_2$-adrenergic receptor stimulating effect with relieved burdens on the heart such as tachycardia.

BACKGROUND ART

As substituted phenylethanolaminotetralin derivatives, for example, compounds represented by the general formula:

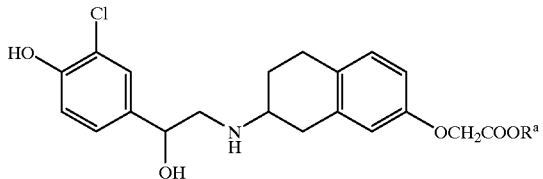

(wherein R$^a$ represents a hydrogen atom or an ethyl group), hydrochloride or oxalate thereof, or single optical isomers thereof which have gut selective sympathomimetic and anti-pollakiuria activities have been disclosed (cf. a published Japanese patent application (kohyo) No. Hei 6-506676 and a published Japanese patent application (kohyo) No. Hei 6-506955). However, these compounds are $\beta_3$-adrenergic receptor stimulating agents having a remarkable $\beta_3$-adrenergic receptor stimulating effect.

In addition, compounds represented by the general formula:

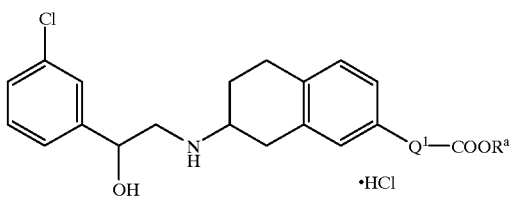

(wherein Q$^1$ represents an ethylene group or a vinylene group; and R$^a$ has the same meaning as defined above) or single optical isomers thereof which have antidepressant and intestine specific motility modulating activities and are useful as antidepressant and intestinal spasmolytic agents have been disclosed (cf. a published Japanese patent application (kokai) No. Hei 5-65254).

DISCLOSURE OF INVENTION

The present invention relates to 3,4-disubstituted phenylethanolaminotetralincarboxylic acid derivatives represented by the general formula:

(I)

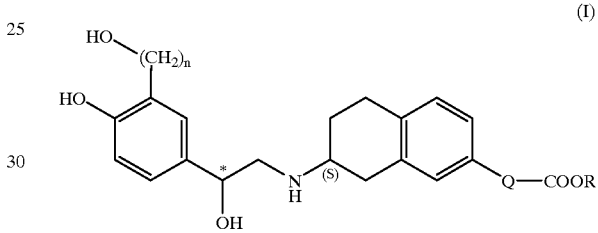

[wherein Q represents a vinylene group or a group represented by the general formula:

-A-(CH$_2$)$_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration] and pharmaceutically acceptable salts thereof.

The present invention relates to a pharmaceutical composition comprising the above 3,4-disubstituted phenylethanolaminotetralincarboxylic acid derivative or a pharmaceutically acceptable salt thereof.

The present invention relates to an agent for the prevention of threatened abortion and premature labor, a bronchodilator and an agent for pain remission and promoting stone removal in urolithiasis which comprises as the active ingredient the above 3,4-disubstituted phenylethanolaminotetralincarboxylic acid derivative or a pharmaceutically acceptable salt thereof.

The present invention relates to a method for the prevention of threatened abortion and premature labor, the prevention and treatment of diseases associated with bronchiostenosis and airway obstruction, and pain remission and promoting stone removal in urolithiasis which comprises administering the above 3,4-disubstituted phenylethanolaminotetralincarboxylic acid derivative or a pharmaceutically acceptable salt thereof.

The present invention relates to a use of the above 3,4-disubstituted phenylethanolaminotetralincarboxylic acid derivative or a pharmaceutically acceptable salt thereof for the manufacture of a pharmaceutical composition for the prevention of threatened abortion and premature labor, the prevention and treatment of diseases associated with bronchiostenosis and airway obstruction, and pain remission and promoting stone removal in urolithiasis.

Furthermore, the present invention relates to a use of the above 3,4-disubstituted phenylethanolaminotetralincarboxylic acid derivative or a pharmaceutically acceptable salt thereof as an agent for the prevention of threatened abortion and premature labor, a bronchodilator and an agent for pain remission and promoting stone removal in urolithiasis.

BEST MODE FOR CARRYING OUT THE INVENTION

In order to find an excellent $\beta_2$-adrenergic receptor stimulating agent, the inventors of the present invention made extensive studies and found that certain 3,4-disubstituted phenylethanolaminotetralincarboxylic acid derivatives represented by the above general formula (I) have a potent and selective $\beta_2$-adrenergic receptor stimulating effect and are remarkably useful as $\beta_2$-adrenergic receptor stimulating agents, thereby forming the basis of the present invention.

Accordingly, the present invention relates to 3,4-disubstituted phenylethanolaminotetralincarboxylic acid derivatives represented by the general formula:

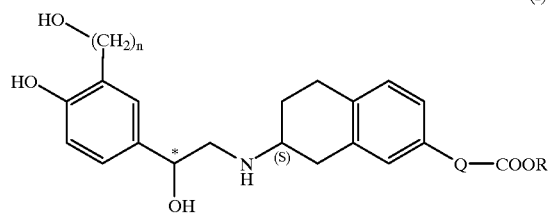

(I)

[wherein Q represents a vinylene group or a group represented by the general formula:

-A-(CH$_2$)$_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration] and pharmaceutically acceptable salts thereof, which have a $\beta_2$-adrenergic receptor stimulating effect with higher selectivity in comparison with a $\beta_1$-adrenergic receptor stimulating effect and with relieved burdens on the heart such as tachycardia.

In the compounds represented by the above general formula (I) of the present invention, the term "lower alkyl group" means a straight or branched-chain alkyl group having 1 to 6 carbon atoms such as a methyl group, an ethyl group, a propyl group and an isopropyl group.

The compounds represented by the above general formula (I) of the present invention can be prepared by the following procedures.

For example, the compounds of the above general formula (I) can be prepared by subjecting an amine compound represented by the general formula:

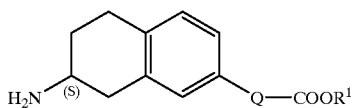

(II)

(wherein $R^1$ is a lower alkyl group; and Q and the carbon atom marked with (S) have the same meanings as defined above) to N-alkylation using an alkylating agent represented by the general formula:

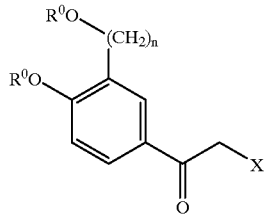

(III)

(wherein $R^0$ is a hydroxy-protective group; X is a halogen atom; and n has the same meaning as defined above), reducing the resulting compound in the usual way, removing the hydroxy-protective group, hydrolyzing the ester group as occasion demands and subjecting the resulting diastereomer mixture obtained to column chromatography or fractional recrystallization in the usual way as occasion demands to isolate the corresponding single isomer.

The compounds represented by the above general formula (I) of the present invention can be also prepared by allowing a mandelic acid derivative represented by the general formula:

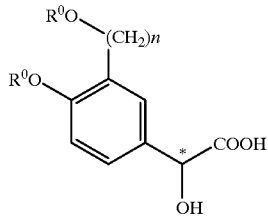

(IV)

(wherein $R^0$, n and the carbon atom marked with * have the same meanings as defined above) to react with an amine compound represented by the above general formula (II) in the presence of a condensing agent to give a compound represented by the general formula:

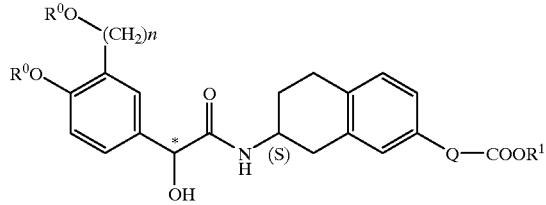

(V)

(wherein Q, $R^0$, $R^1$, n, the carbon atom marked with * and the carbon atom marked with (S) have the same meanings as defined above), reducing the resulting compound using an appropriate reducing agent to prepare a compound represented by the general formula:

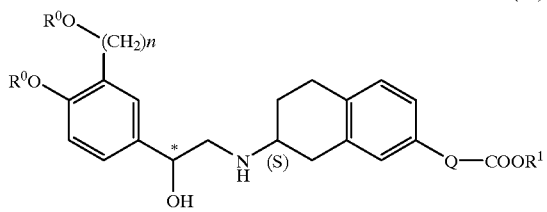
(VI)

(wherein Q, R⁰, R¹, n, the carbon atom marked with * and the carbon atom marked with (S) have the same meanings as defined above), removing the hydroxy-protective group, and hydrolyzing the ester group as occasion demands.

Of the compounds represented by the above general formula (I) of the present invention, compounds represented by the general formula:

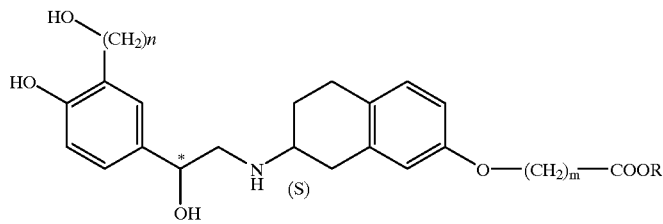

(wherein R, m, n, the carbon atom marked with * and the carbon atom marked with (S) have the same meanings as defined above) can be prepared by allowing a mandelic acid derivative represented by the above general formula (IV) to react with an amine compound represented by the formula:

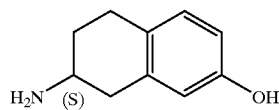
(VII)

(wherein the carbon atom marked with (S) has the same meaning as defined above) in the presence of a condensing agent to give a compound represented by the general formula:

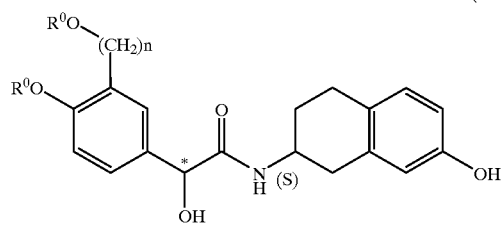
(VIII)

(wherein R⁰, n, the carbon atom marked with * and the carbon atom marked with (S) have the same meanings as defined above), reducing the resulting compound using a reagent such as borane-dimethylsulfide complex to prepare a compound represented by the general formula:

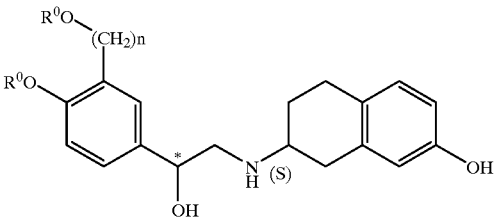
(IX)

(wherein R⁰, n, the carbon atom marked with * and the carbon atom marked with (S) have the same meanings as defined above), protecting the alcoholic hydroxy group and amino group with a reagent such as trifluoroacetic anhydride as occasion demands, subjecting the resulting compound to O-alkylation of the phenolic hydroxy group using an alkylating agent represented by the general formula:

(X)

(Ia)

(wherein R¹, X and m have the same meanings as defined above), removing the protective group, and hydrolyzing the ester group as occasion demands.

Among the compounds represented by the above general formula (I) of the present invention, single isomers can be also prepared by subjecting a diastereomer mixture obtained as an intermediate in the aforementioned production processes to column chromatography or fractional recrystallization to isolate the corresponding single isomer and then carrying out the same reaction using said single isomer.

Of the amine compounds represented by the above general formula (II) which are used as starting materials in the aforementioned production process, compounds represented by the general formula:

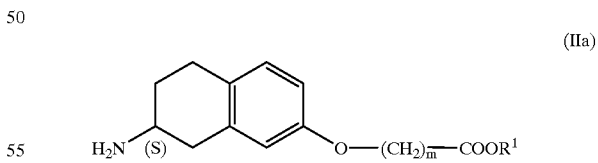
(IIa)

(wherein R¹, m and the carbon atom marked with (S) have the same meanings as defined above) can be prepared by processes described in literatures or analogous processes thereto (for example, *Eur. J. Med. Chem.*, No. 29, pp. 259–267 (1994); a published Japanese patent application (Kokai) No. Hei 3-14548).

Of the amine compounds represented by the above general formula (II) which are used as starting materials in the aforementioned production process, compounds represented by the general formula:

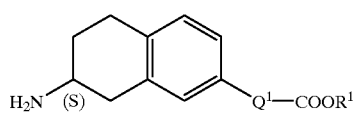
(IIb)

(wherein $Q^1$ represents a vinylene group or an ethylene group; and $R^1$ and the carbon atom marked with (S) have the same meanings as defined above) can be prepared by allowing a compound represented by the general formula:

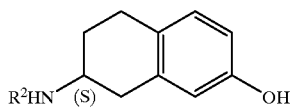
(XI)

(wherein $R^2$ represents an amino-protective group; and the carbon atom marked with (S) has the same meaning as defined above) to react with trifluoromethanesulfonic anhydride in an inert solvent to give a sulfonic acid derivative represented by the general formula:

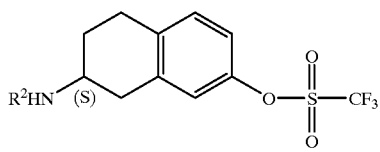
(XII)

(wherein $R^2$ and the carbon atom marked with (S) have the same meanings as defined above), allowing the resulting compound to react with an unsaturated carboxylate compound represented by the general formula:

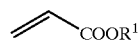
(XII)

(wherein $R^1$ has the same meaning as defined above) in the presence of a palladium reagent, triphenylphosphine and a base to prepare a compound represented by the general formula:

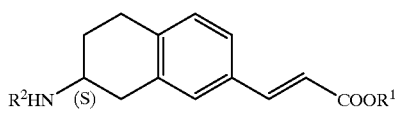
(XIV)

(wherein $R^1$, $R^2$ and the carbon atom marked with (S) have the same meanings as defined above), reducing the resulting compound in the usual way as occasion demands and removing the amino-protective group.

Of the amine compounds represented by the above general formula (II) which are used as starting materials in the aforementioned production process, compounds represented by the general formula:

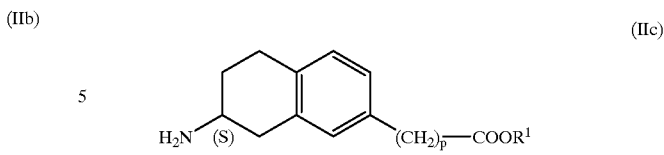
(IIc)

(wherein p is an integer of from 3 to 7; and $R^1$ and the carbon atom marked with (S) have the same meanings as defined above) can be prepared by allowing a sulfonic acid derivative represented by the above general formula (XII) to react with an unsaturated carboxylate compound represented by the general formula:

(XV)

(wherein q is an integer of from 1 to 5; and $R^1$ has the same meaning as defined above) in the presence of 9-borabicyclo-[3.3.1]nonane, tetrakis(triphenylphosphine)palladium(0) and potassium phosphate in an inert solvent, and removing the amino-protective group.

Of the alkylating agents represented by the above general formula (III) which are used as starting materials in the aforementioned production processes, compounds wherein n is 1 can be prepared, for example, by allowing a ketone compound represented by the formula:

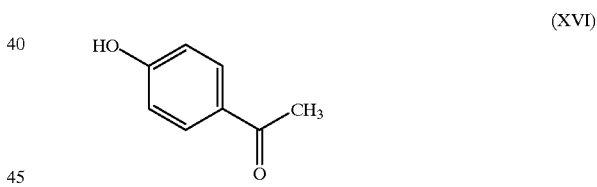
(XVI)

to react with formalin in the presence of hydrochloric acid to prepare a compound represented by the formula:

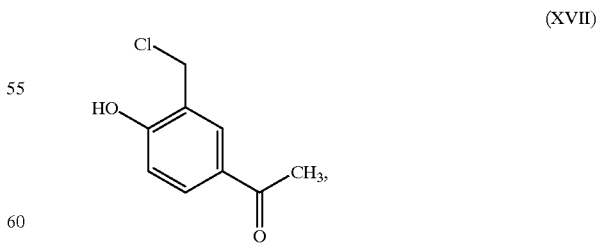
(XVII)

treating the resulting compound with acetic anhydride and sodium acetate to give a compound represented by the formula:

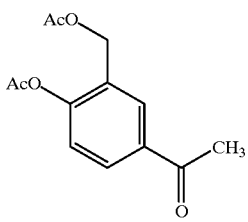

(XVIII)

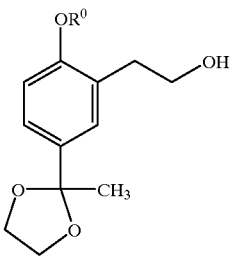

(XXI)

(wherein Ac represents an acetyl group), subjecting the resulting compound to halogenation in the usual way using a halogenating agent, subjecting the resulting halogeno compound (the corresponding bromo compound is described in *J. Med. Chem.*, No. 13, pp. 674–680 (1970)) represented by the general formula:

(wherein $R^0$ has the same meaning as defined above), protecting the hydroxy group of the resulting compound using a reagent such as benzyl bromide, removing the carbonyl-protective group to prepare a compound represented by the general formula:

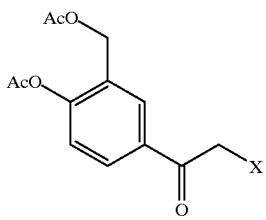

(XIX)

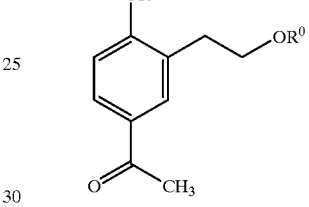

(XXII)

(wherein Ac and X have the same meanings as defined above) to deacetylation in the usual way and introducing a protective group to the hydroxy group using a reagent such as acetone dimethyl acetal.

Of the alkylating agents represented by the above general formula (III) which are used as starting materials in the aforementioned production processes, compounds wherein n is 2 can be prepared by protecting the hydroxy group of a phenylacetate derivative represented by the general formula:

(wherein $R^0$ has the same meaning as defined above) and then subjecting the resulting compound to halogenation in the usual way using a halogenating agent.

The phenylacetate derivatives represented by the above general formula (XX) which are used as starting materials in the aforementioned production process can be prepared by processes described in literatures or analogous processes thereto (for example, a published Japanese patent application (kohyo) No. Sho 61-500915, a published Japanese patent application (kokai) No. Sho 57-135049).

The mandelic acid derivatives represented by the above general formula (IV) which are used as starting materials in the aforementioned production process can be prepared by allowing a bromo compound represented by the general formula:

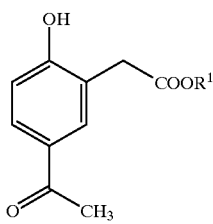

(XX)

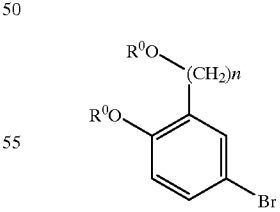

(XXIII)

(wherein $R^1$ has the same meaning as defined above) in the usual way using a reagent such as benzyl bromide, further protecting the carbonyl group using ethylene glycol and then reducing the resulting compound in the usual way using a reducing agent such as lithium aluminum hydride to prepare an alcohol compound represented by the general formula:

(wherein $R^0$ and n have the same meanings as defined above), which can be obtained in accordance with processes described in literatures or analogous processes thereto, to react with diethyl oxalate, reducing the resulting phenylglyoxylic acid derivative using a reagent such as sodium borohydride, hydrolyzing the ester compound to give a mandelic acid derivative represented by the general formula:

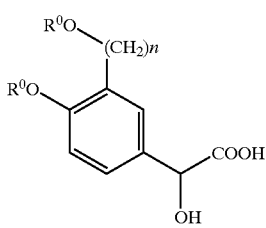

(XXIV)

(wherein $R^0$ and n have the same meanings as defined above) and subjecting the derivative to optical resolution in the usual way using a resolving reagent such as optically active 1-(1-naphthyl)ethylamine or phenylalaninol as occasion demands.

The compounds of the present invention obtained by the aforementioned production processes can be easily isolated and purified by conventional separation means such as fractional recrystallization, purification using column chromatography, solvent extraction and the like.

The 3,4-disubstituted phenylethanolaminotetralin-carboxylic acid derivative represented by the above general formula (I) of the present invention can be converted into its pharmaceutically acceptable salts in the usual way. Examples of such salts include acid addition salts with mineral acids (e.g., hydrochloric acid, hydrobromic acid, hydroiodic acid, sulfuric acid, nitric acid, phosphoric acid and the like), acid addition salts with organic acids (e.g., formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like), salts with inorganic bases such as a sodium salt and a potassium salt, salts with organic bases (e.g., morpholine, piperidine and the like) and salts with amino acids. The resulting salts have the same pharmacological activities as those of the free forms.

In addition, the compounds represented by the above general formula (I) of the present invention also include hydrates thereof and solvates thereof with pharmaceutically acceptable solvents (e.g., ethanol).

Of the compounds represented by the above general formula (I) of the present invention, compounds having an unsaturated bond exist in two geometrical isomer forms. The present invention includes either one of cis isomer or trans isomer.

The compounds represented by the above general formula (I) of the present invention exist in two isomer forms of R configuration and S configuration based on the asymmetric carbon atom having the hydroxy group. Either one of the isomers or a mixture thereof can be used in the present invention.

When the in vitro test for measuring $\beta_2$-adrenergic receptor stimulating activity was carried out in the usual way using isolated rat pregnant uterus, the compounds represented by the above general formula (I) of the present invention showed an activity to relax 50% of the spontaneous contractions of rat myometrium (i.e., $EC_{50}$ value) at an approximate mol concentration of $1.0 \times 10^{-9}$ to $5.0 \times 10^{-7}$. For example, ethyl 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate showed the $EC_{50}$ value at a mol concentration of $1.1 \times 10^{-9}$. Thus, the compounds of the present invention have markedly potent $\beta_2$-adrenergic receptor stimulating effect and therefore are remarkably useful as $\beta_2$-adrenergic receptor stimulating agents.

When the in vitro test for measuring $\beta_1$-adrenergic receptor stimulating activity was carried out in the usual way using isolated rat atrium, the compounds represented by the above general formula (I) of the present invention showed an activity to increase 20 beats per minute of rat heart rate by the spontaneous motility of myocardium (i.e., $EC_{20}$ value) at an approximate mol concentration of $5.0 \times 10^{-7}$ or more. For example, ethyl 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate showed the $EC_{20}$ value at a mol concentration of $1.1 \times 10^{-6}$. Thus, the compounds of the present invention have markedly weak $\beta_1$-adrenergic receptor stimulating effect in comparison with the aforementioned $\beta_2$-adrenergic receptor stimulating effect.

In consequence, the compounds of the present invention have markedly potent $\beta_2$-adrenergic receptor stimulating effect with markedly high selectivity in comparison with $\beta_1$-adrenergic receptor stimulating effect, so that these are a extremely useful and selective $\beta_2$-adrenergic receptor stimulating agents of in which burdens on the heart are reduced due to suppression of side effects upon the heart (e.g., tachycardia) caused by $\beta_1$-adrenergic receptor stimulating effect.

The present invention relates to a selective $\beta_2$-adrenergic receptor stimulating agent which is extremely useful as, for example, an agent for the prevention of threatened abortion, premature labor, a bronchodilator (an agent for the prevention and treatment of diseases associated with bronchiostenosis and airway obstruction) and an agent for pain remission or promoting stone removal in urolithiasis.

When the 3,4-disubstituted phenylethanolaminotetralin-carboxylic acid derivatives represented by the above general formula (I) of the present invention and pharmaceutically acceptable salts thereof are used in the practical treatment, they are administered orally or parenterally in the form of appropriate pharmaceutical compositions such as tablets, powders, fine granules, granules, capsules, injections and the like. These pharmaceutical compositions can be formulated in accordance with conventional methods using conventional pharmaceutical carriers, excipients and other additives.

The dose is appropriately decided depending on the sex, age, body weight, degree of symptoms and the like of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

EXAMPLE

The contents of the present invention are described further in detail with reference to the following Reference Examples, Examples and Test Examples, but the present invention is not limited thereto. All melting points of the compounds described in Reference Examples and Examples were uncorrected.

REFERENCE EXAMPLE 1

2-Bromo-1-(2,2-dimethylbenzo[1,2-d]-1,3-dioxan-6-yl)-1-ethanone

2-Acetoxymethyl-4-bromoacetylphenyl acetate (18.6 g) was dissolved in methanol (90 ml), and 47% hydrobromic acid (100 ml) was added to the solution under ice-cooling with stirring. After reaction for 16 hours at room temperature, water was added to the reaction mixture under ice-cooling with stirring, and the precipitates were collected by filtration and washed with water and hexane to give 2-bromo-4'-hydroxy-3'-hydroxymethylacetophenone (9.54 g) having a melting point of 117–119° C.

IR (KBr): 3440, 1677 cm$^{-1}$ $^1$H-NMR (DMSO-d$_6$) δ ppm: 4.50 (2H, s), 4.75 (2H, s), 5.10 (1H, br s), 6.87 (1H, d, J=8.5 Hz), 7.79 (1H, dd, J=8.5, 2.4 Hz), 7.99 (1H, d, J=2.4 Hz), 10.52 (1H, s)

2-Bromo-4'-hydroxy-3'-hydroxymethylacetophenone (17.7 g), p-toluenesulfonic acid monohydrate (124 mg) and acetone dimethyl acetal (256 ml) were dissolved in acetone (256 ml), and the solution was heated under reflux for 30 minutes. After cooling, a saturated aqueous sodium bicarbonate solution was added to the reaction mixture, and the resulting mixture was extracted with ethyl acetate. The extract was washed with water and brine, and dried over anhydrous magnesium sulfate, then the solvent was removed in vacuo. Purification of the residue by medium pressure liquid column chromatography on silica gel (eluent: hexane/ethyl acetate=7/1) gave 2-bromo-1-(2,2-dimethylbenzo[1,2-d]-1,3-dioxan-6-yl)-1-ethanone (11.9 g) having a melting point of 52–54° C.

IR (KBr): 1693 cm$^{-1}$ $^1$H-NMR (CDCl$_3$) δ ppm: 1.57 (6H, s), 4.37 (2H, s), 4.89 (2H, s), 6.88 (1H, d, J=8.6 Hz), 7.69 (1H, d, J=2.2 Hz), 7.82 (1H, dd, J=8.6, 2.2 Hz)

REFERENCE EXAMPLE 2

Ethyl (S)-5-(2-amino-1,2,3,4-tetrahydronaphthalen-7-yloxy)valerate Hydrochloride (S)-2-(tert-Butoxycarbonylamino)-7-hydroxytetralin (700 mg) was dissolved in acetone (14 ml), and ethyl 5-bromo-valerate (635 μl) and potassium carbonate (1.11 g) were added to the solution, then the resulting mixture was heated under reflux for 20 hours. After cooling, the insoluble material was filtered off, and the filtrate was concentrated in vacuo. The residue was dissolved in diethyl ether, washed with water and brine and dried over anhydrous magnesium sulfate, then the solvent was removed in vacuo. The residue was dissolved in 2.8 M hydrogen chloride ethanol solution (1.91 ml), followed by reaction for 28 hours at room temperature, and the reaction mixture was concentrated in vacuo. Recrystallization of the residue from diethyl ether gave ethyl (S)-5-(2-amino-1,2,3,4-tetrahydronaphthalen-7-yloxy)valerate hydrochloride (743 mg) having a melting point of 136–139° C.

IR (KBr): 3453, 2358, 1730 cm$^{-1}$ $^1$H-NMR (CDCl$_3$) δ ppm: 1.17 (3H, t, J=7.1 Hz), 1.60–1.80 (5H, m), 2.05–2.15 (1H, m), 2.35 (2H, t, J=7.0 Hz), 2.65–2.85 (3H, m), 3.03 (1H, dd, J=16.6, 5.1 Hz), 3.25–3.45 (1H, m), 3.91 (2H, t, J=5.9 Hz), 4.05 (2H, q, J=7.1 Hz), 6.65–6.75 (2H, m), 7.00 (1H, d, J=8.3 Hz), 8.16 (3H, br)

Specific rotation: [α]$_D^{25}$=−42.9° (c=0.49, MeOH)

REFERENCE EXAMPLE 3

Ethyl (S)-3-(2-amino-1,2,3,4-tetrahydronaphthalen-7-yl)acrylate (S)-2-(tert-Butoxycarbonylamino)-7-hydroxytetralin (1.47 g) and 4-dimethylaminopyridine (1.36 g) were dissolved in dichloromethane (75 ml), and trifluoromethanesulfonic anhydride (1.03 ml) was added to the solution under ice-cooling with stirring, then the resulting mixture was stirred for 30 minutes. The reaction mixture was washed with 0.17 N hydrochloric acid and 0.5 M aqueous phosphate buffer solution (pH 7) sequentially, and dried over anhydrous magnesium sulfate, then the solvent was removed in vacuo. Purification of the residue by medium pressure liquid column chromatography on silica gel (eluent: hexane/ethyl acetate=9/1) gave (S)-2-(tert-butoxycarbonylamino)-1,2,3,4-tetrahydronaphthalen-7-yl trifluoromethanesulfonate (1.82 g) as an oil.

IR (neat): 3332, 1696 cm$^{-1}$ $^1$H-NMR (CDCl$_3$) δ ppm: 1.46 (9H, s), 1.70–1.85 (1H, m), 2.00–2.15 (1H, m), 2.65 (1H, dd, J=16.5, 8.4 Hz), 2.88 (2H, t, J=6.6 Hz), 3.14 (1H, dd, J=16.5, 5.0 Hz), 3.90–4.05 (1H, m), 4.45–4.65 (1H, m), 6.97 (1H, d, J=2.6 Hz), 7.02 (1H, dd, J=8.5, 2.6 Hz), 7.15 (1H, d, J=8.5 Hz)

Specific rotation: [α]$_D^{25}$=−43.7° (c=1.10, MeOH)

(S)-2-(tert-Butoxycarbonylamino)-1,2,3,4-tetrahydronaphthalen-7-yl trifluoromethanesulfonate (500 mg), ethyl acrylate (179 μl), triphenylphosphine (22 mg), palladium acetate (9.3 mg) and triethylamine (250 μl) were allowed to react for 6 hours at 90° C. and for 5 hours at 100° C. with stirring. Ethyl acrylate (97 μl), triethylamine (125 μl) and bis(triphenylphosphine)palladium(II) dichloride (27 mg) were added to the reaction mixture, followed by reaction for 11 hours at 100° C. with stirring. Water was added to the reaction mixture, and the resulting mixture was extracted with ethyl acetate. The extract was washed with 1 N hydrochloric acid and 0.5 M aqueous phosphate buffer solution (pH 7) sequentially, and dried over anhydrous magnesium sulfate, then the solvent was removed in vacuo. Purification by medium pressure liquid column chromatography on silica gel (eluent: dichloromethane/ethyl acetate=20/1) and sequential recrystallization from diisopropyl ether of the residue gave ethyl (S)-3-[2-(tert-butoxycarbonylamino)-1,2,3,4-tetrahydronaphthalen-7-yl]acrylate (252 mg) having a melting point of 99–100° C.

IR (KBr): 3356, 1710, 1679 cm$^{-1}$ $^1$H-NMR (CDCl$_3$) δ ppm: 1.33 (3H, t, J=7.1 Hz), 1.46 (9H, s), 1.70–1.80 (1H, m), 2.00–2.15 (1H, m), 2.63 (1H, dd, J=16.4, 8.4 Hz), 2.88 (2H, t, J=6.6 Hz), 3.12 (1H, dd, J=16.4, 5.1 Hz), 3.90–4.05 (1H, m), 4.26 (2H, q, J=7.1 Hz), 4.45–4.60 (1H, m), 6.38 (1H, d, J=16.0 Hz), 7.10 (1H, d, J=7.9 Hz), 7.21 (1H, s), 7.29 (1H, d, J=7.9 Hz), 7.62 (1H, d, J=16.0 Hz)

Specific rotation: [α]$_D^{25}$=−79.2° (c=1.03, MeOH)

Ethyl (S)-3-[2-(tert-butoxycarbonylamino)-1,2,3,4-tetrahydronaphthalen-7-yl]acrylate (516 mg) was dissolved in ethanol (10 ml), and 3 M hydrogen chloride ethanol solution (2 ml) was added to the solution at room temperature with stirring. After reaction for 13 hours, the reaction mixture was concentrated in vacuo. A saturated aqueous sodium bicarbonate solution (20 ml) and dichloromethane (5 ml) were added to the residue, and the resulting mixture was stirred for an hour at room temperature. Water was added to the reaction mixture, and the resulting mixture was extracted with dichloromethane. The extract was washed with water and dried over anhydrous magnesium sulfate. Removal of the solvent in vacuo gave ethyl (S)-3-(2-amino-1,2,3,4-tetrahydronaphthalen-7-yl)acrylate (366 mg) as an oil.

IR (neat): 3356, 1708, 1638 cm$^{-1}$ $^1$H-NMR (CDCl$_3$) δ ppm: 1.20–1.40 (5H, m), 1.50–1.70 (1H, m), 1.95–2.10 (1H, m), 2.56 (1H, dd, J=16.2, 9.3 Hz), 2.80–2.95 (2H, m), 3.00 (1H, dd, J=16.2, 3.9 Hz), 3.15–3.30 (1H, m), 4.25 (2H, q, J=7.1 Hz), 6.39 (1H, d, J=16.0 Hz), 7.10 (1H, d, J=7.9 Hz), 7.20–7.35 (2H, m), 7.63 (1H, d, J=16.0 Hz)

Specific rotation: [α]$_D^{25}$=−54.5° (c=1.03, CHCl$_3$)

REFERENCE EXAMPLE 4

Ethyl (S)-3-(2-amino-1,2,3,4-tetrahydronaphthalen-7-yl)propionate

Ethyl (S)-3-[2-(tert-butoxycarbonylamino)-1,2,3,4-tetrahydronaphthalen-7-yl]acrylate (252 mg) was dissolved in ethanol (10 ml), and 10% palladium on activated carbon (30 mg) was added to the solution, then the resulting mixture was stirred for 3 hours at room temperature under a hydrogen atmosphere. The reaction mixture was filtrated to remove the catalyst, and the filtrate was concentrated in vacuo. Recrystallization of the residue from diisopropyl ether gave ethyl (S)-3-[2-(tert-butoxycarbonylamino)-1,2,3,4-tetrahydronaphthalen-7-yl]propionate (236 mg) having a melting point of 101–102° C.

IR (KBr): 3363, 1732, 1680 cm$^{-1}$ $^1$H-NMR (CDCl$_3$) δ ppm: 1.24 (3H, t, J=7.1 Hz), 1.45 (9H, s), 1.65–1.80 (1H, m), 2.00–2.10 (1H, m), 2.50–2.65 (3H, m), 2.75–2.95 (4H, m), 3.07 (1H, dd, J=15.8, 4.5 Hz), 3.85–4.00 (1H, m), 4.13 (2H, q, J=7.1 Hz), 4.50–4.65 (1H, m), 6.90 (1H, s), 6.96 (1H, d, J=7.9 Hz), 7.01 (1H, d, J=7.9 Hz)

Specific rotation: $[α]_D^{25}$=−47.8° (c=1.03, MeOH)

Ethyl (S)-3-[2-(tert-butoxycarbonylamino)-1,2,3,4-tetrahydronaphthalen-7-yl]propionate (1.47 g) was dissolved in ethanol (21 ml), and 3 M hydrogen chloride ethanol solution (4 ml) was added to the solution at room temperature with stirring. After reaction for 20 hours, the reaction mixture was concentrated in vacuo. A saturated aqueous sodium bicarbonate solution (50 ml) and dichloromethane (10 ml) were added to the residue, and the resulting mixture was stirred for an hour at room temperature. Water was added to the reaction mixture, and the resulting mixture was extracted with dichloromethane. The extract was washed with water and dried over anhydrous magnesium sulfate. Removal of the solvent in vacuo gave ethyl (S)-3-(2-amino-1,2,3,4-tetrahydronaphthalen-7-yl)propionate (1.05 g) as an oil.

IR (neat): 3353, 3289, 1733 cm$^{-1}$ $^1$H-NMR (CDCl$_3$) δ ppm: 1.25 (3H, t, J=7.1 Hz), 1.43 (2H, br s), 1.50–1.65 (1H, m), 1.95–2.05 (1H, m), 2.45–2.65 (3H, m), 2.75–2.95 (4H, m), 2.96 (1H, dd, J=16.2, 4.8 Hz), 3.10–3.25 (1H, m), 4.13 (2H, q, J=7.1 Hz), 6.91 (1H, s), 6.95 (1H, d, J=7.8 Hz), 7.02 (1H, d, J=7.8 Hz)

Specific rotation: $[α]_D^{25}$=−53.9° (c=1.03, CHCl$_3$)

REFERENCE EXAMPLE 5

Ethyl (S)-5-(2-amino-1,2,3,4-tetrahydronaphthalen-7-yl)valerate

Ethyl 4-pentenoate (317 mg) was dissolved in tetrahydrofuran (5 ml), and 9-borabicyclo[3.3.1]nonane (302 mg) was added to the solution. After reaction for 15 hours at room temperature with stirring, 1,4-dioxane (9 ml), (S)-2-(tert-butoxycarbonylamino)-1,2,3,4-tetrahydronaphthalen-7-yl trifluoromethanesulfonate (890 mg), tetrakis (triphenylphosphine)palladium (0) (65 mg) and potassium phosphate (716 mg) were added to the reaction mixture, followed by reaction for 15 hours at 85° C. with stirring. Water was added to the reaction mixture, and the resulting mixture was extracted with ethyl acetate. The extract was washed with water and dried over anhydrous magnesium sulfate, then the solvent was removed in vacuo. Purification by medium pressure liquid column chromatography on silica gel (eluent: dichloromethane) and sequential recrystallization from hexane of the residue gave ethyl (S)-5-[2-(tert-butoxycarbonylamino)-1,2,3,4-tetrahydronaphthalen-7-yl] valerate (387 mg) having a melting point of 65–67° C.

IR (KBr): 3365, 1733, 1681 cm$^{-1}$ $^1$H-NMR (CDCl$_3$) δ ppm: 1.25 (3H, t, J=7.1 Hz), 1.45 (9H, s), 1.55–1.80 (5H, m), 2.00–2.10 (1H, m), 2.32 (2H, t, J=7.2 Hz), 2.50–2.65 (3H, m), 2.80–2.90 (2H, m), 3.08 (1H, dd, J=16.1, 5.0 Hz), 3.90–4.05 (1H, m), 4.12 (2H, q, J=7.1 Hz), 4.50–4.65 (1H, m), 6.89 (1H, s), 6.93 (1H, d, J=7.9 Hz), 7.00 (1H, d, J=7.9 Hz)

Specific rotation: $[α]_D^{25}$=−52.2° (c=1.16, MeOH)

Ethyl (S)-5-[2-(tert-butoxycarbonylamino)-1,2,3,4-tetrahydronaphthalen-7-yl]valerate (687 mg) was dissolved in ethanol (10 ml), and 3 M hydrogen chloride ethanol solution (3 ml) was added to the solution at room temperature with stirring. After reaction for 15 hours, the reaction mixture was concentrated in vacuo. A saturated aqueous sodium bicarbonate solution (10 ml) and dichloromethane (5 ml) were added to the residue, and the resulting mixture was stirred for an hour at room temperature. Water was added to the reaction mixture, and the resulting mixture was extracted with dichloromethane. The extract was washed with water and dried over anhydrous magnesium sulfate. Removal of the solvent in vacuo gave ethyl (S)-5-(2-amino-1,2,3,4-tetrahydronaphthalen-7-yl)valerate (509 mg) as an oil.

IR (neat): 3357, 3294, 1736 cm$^{-1}$ $^1$H-NMR (CDCl$_3$) δ ppm: 1.25 (3H, t, J=7.1 Hz), 1.34 (2H, br s), 1.50–1.75 (5H, m), 1.95–2.05 (1H, m), 2.32 (2H, t, J=7.1 Hz), 2.45–2.60 (3H, m), 2.75–2.95 (2H, m), 2.96 (1H, dd, J=15.9, 4.3 Hz), 3.10–3.25 (1H, m), 4.12 (2H, q, J=7.1 Hz), 6.88 (1H, s), 6.92 (1H, d, J=7.7 Hz), 7.00 (1H, d, J=7.7 Hz)

Specific rotation: $[α]_D^{25}$=−46.5° (c=1.10, CHCl$_3$)

REFERENCE EXAMPLE 6

Ethyl (S)-6-(2-amino-1,2,3,4-tetrahydronaphthalen-7-yl)hexanoate

Ethyl (S)-6-(2-amino-1,2,3,4-tetrahydronaphthalen-7-yl) hexanoate as an oil was prepared according to a similar manner to that described in Reference Example 5 using ethyl 5-hexenoate instead of ethyl 4-pentenoate.

IR (neat): 3361, 3295, 1729 cm$^{-1}$ $^1$H-NMR (CDCl$_3$) δ ppm: 1.25 (3H, t, J=7.1 Hz), 1.30–1.75 (9H, m), 1.90–2.05 (1H, m), 2.29 (2H, t, J=7.6 Hz), 2.45–2.60 (3H, m), 2.75–2.95 (2H, m), 2.96 (1H, dd, J=16.0, 4.7 Hz), 3.10–3.25 (1H, m) 4.12 (2H, q, J=7.1 Hz), 6.88 (1H, s), 6.92 (1H, d, J=7.8 Hz), 7.00 (1H, d, J=7.8 Hz)

Specific rotation: $[α]_D^{25}$=−47.7° (c=1.01, CHCl$_3$)

REFERENCE EXAMPLE 7

Ethyl 5-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]valerate Ethyl (S)-5-(2-amino-1,2,3,4-tetrahydronaphthalen-7-yloxy)valerate hydrochloride (743 mg) was dissolved in ethanol (7 ml), and potassium carbonate (313 mg) was added to the solution under ice-cooling, then the resulting mixture was stirred for an hour at room temperature. The insoluble material was filtered off, and the filtrate was concentrated in vacuo. The residue was dissolved in N,N-dimethylformamide (3 ml), and 2-bromo-1-(2,2- dimethylbenzo[1,2-d]-1,3-dioxan-6-yl)ethanone (291 mg) was added to the solution under ice-cooling with stirring, followed by reaction for 35 minutes. Sodium borohydride (193 mg) and ethanol (6 ml) were added to the reaction mixture under ice-cooling with stirring. After reaction for 35 minutes, the reaction mixture was poured into ice-water and extracted with ethyl acetate. The extract was washed with water and dried over anhydrous magnesium sulfate, and the solvent was removed in vacuo. A solution of triethanolamine (304 mg) in tetrahydrofuran (3 ml) was added to the residue, and the resulting mixture was heated under reflux for 12 hours. The reaction mixture was concentrated in vacuo, and the residue was dissolved in ethyl acetate. The resulting mixture was washed with water and dried over anhydrous magnesium sulfate, and the solvent was removed in vacuo. Purification of the residue by medium pressure liquid column chromatography on silica gel (eluent: chloroform/ethanol=10/1) gave ethyl 5-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]valerate (208 mg) as an amorphous.

IR (KBr): 3150, 1733 cm$^{-1}$ $^1$H-NMR (CDCl$_3$) δ ppm: 1.26 (3H, t, J=7.1 Hz), 1.40–1.70 (9H, m), 1.75–1.90 (4H, m), 2.00–2.15 (1H, m), 2.35–2.45 (2H, m), 2.50–3.20 (7H, m), 3.90–4.00 (2H, m), 4.13 (2H, q, J=7.1 Hz), 4.55–4.65 (1H, m), 4.85 (2H, s), 6.59 (1H, d, J=2.6 Hz), 6.67 (1H, dd, J=8.4, 2.6 Hz), 6.80 (1H, d, J=8.4 Hz), 6.98 (1H, d, J=8.4 Hz), 7.02 (1H, d, J=1.8 Hz), 7.14 (1H, dd, J=8.4, 1.8 Hz)

REFERENCE EXAMPLE 8

The following compounds were prepared according to a similar manner to that described in Reference Example 7 using the corresponding ester compound instead of ethyl (S)-5-(2-amino-1,2,3,4-tetrahydronaphthalen-7-yloxy) valerate.

Ethyl 2-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]acetate Amorphous IR (KBr): 3304, 1758, 1737 cm$^{-1}$ $^1$H-NMR (CDCl$_3$) δ ppm: 1.30 (3H, t, J=7.1 Hz), 1.45–1.70 (7H, m), 2.00–2.10 (1H, m), 2.50–3.10 (7H, m), 4.27 (2H, q, J=7.1 Hz), 4.55–4.65 (3H, m), 4.84 (2H, s), 6.61 (1H, s), 6.69 (1H, dd, J=8.4, 2.6 Hz), 6.79 (1H, d, J=8.4 Hz), 6.99 (1H, d, J=8.4 Hz), 7.02 (1H, s), 7.13 (1H, d, J=8.4 Hz)

Ethyl 3-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yl]acrylate Amorphous IR (film): 3300, 1709, 1637 cm$^{-1}$ $^1$H-NMR (CDCl$_3$) δ ppm: 1.33 (3H, t, J=7.1 Hz), 1.50–1.75 (7H, m), 2.00–2.15 (1H, m), 2.55–3.10 (7H, m), 4.26 (2H, q, J=7.1 Hz), 4.55–4.65 (1H, m), 4.85 (2H, s), 6.38 (1H, d, J=16.0 Hz), 6.80 (1H, d, J=8.4 Hz), 7.02 (1H, d, J=1.6 Hz), 7.05–7.35 (4H, m), 7.63 (1H, d, J=16.0 Hz)

Ethyl 3-[(2S)-2-[[(2RS)-2-(2,2-dimethylbenzo[1,2-d]-1,3-dioxan-6-yl)-2-hydroxyethyl]amino]-1,2,3,4-tetrahydronaphthalen- 7-yl]propionate Amorphous IR (KBr): 3165, 1729 cm$^{-1}$ $^1$H-NMR (CDCl$_3$) δ ppm: 1.25 (3H, t, J=7.1 Hz), 1.50–1.70 (7H, m), 2.00–2.15 (1H, m), 2.50–3.10 (11H, m), 4.13 (2H, q, J=7.1 Hz), 4.55–4.65 (1H, m), 4.85 (2H, s), 6.80 (1H, d, J=8.4 Hz), 6.85–7.05 (4H, m), 7.10–7.20 (1H, m)

Ethyl 5-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yl]valerate Amorphous IR (KBr): 3149, 1738 cm$^{-1}$ $^1$H-NMR (CDCl$_3$) δ ppm: 1.25 (3H, t, J=7.1 Hz), 1.50–1.75 (11H, m), 2.00–2.15 (1H, m), 2.32 (2H, t, J=7.1 Hz), 2.50–3.10 (9H, m), 4.12 (2H, q, J=7.1 Hz), 4.55–4.65 (1H, m), 4.85 (2H, s), 6.80 (1H, d, J=8.4 Hz), 6.85–7.10 (4H, m), 7.14 (1H, dd, J=8.4, 1.6 Hz)

Ethyl 6-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yl]hexanoate Amorphous IR (KBr): 3302, 1736 cm$^{-1}$ $^1$H-NMR (CDCl$_3$) δ ppm: 1.24 (3H, t, J=7.1 Hz), 1.30–1.45 (2H, m), 1.50–1.75 (11H, m), 2.00–2.15 (1H, m), 2.29 (2H, t, J=7.5 Hz), 2.45–3.10 (9H, m), 4.12 (2H, q, J=7.1 Hz), 4.55–4.65 (1H, m), 4.85 (2H, s), 6.80 (1H, d, J=8.3 Hz), 6.85–7.05 (4H, m), 7.14 (1H, dd, J=8.3, 2.1 Hz)

REFERENCE EXAMPLE 9

Ethyl 2-[(2S)-2-[[(2RS)-2-[4-benzyloxy-3-(2-benzyloxyethyl)phenyl]-2-hydroxyethyl]amino]-1,2,3,4-tetrahydronaphthalen-7-yloxy]acetate Methyl 2-(5-acetyl-2-hydroxyphenyl)acetate (8.0 g) was dissolved in N,N-dimethylformamide (120 ml), and benzyl bromide (5 ml) and potassium carbonate (5.8 g) were added to the solution, then the resulting mixture was stirred for 16 hours at room temperature. Ice (ca. 100 g) and hexane (200 ml) were added to the reaction mixture, and water (200 ml) was added to the resulting mixture with vigorously stirring. The precipitated crystal was collected by filtration and recrystallized from dichloromethane-hexane to give methyl 2-(5-acetyl-2-benzyloxyphenyl)acetate (10.1 g) having a melting point of 85–87° C.

IR (KBr): 1747, 1682 cm$^{-1}$ $^1$H-NMR (CDCl$_3$) δ ppm: 2.55 (3H, s), 3.64 (3H, s), 3.71 (2H, s), 5.16 (2H, s), 6.96 (1H, d, J=8.6 Hz), 7.30–7.40 (5H, m), 7.85 (1H, d, J=2.3 Hz), 7.89 (1H, dd, J=8.6, 2.3 Hz)

Methyl 2-(5-acetyl-2-benzyloxyphenyl)acetate (9.0 g), methyl orthoformate (18 ml) and ethylene glycol (18 ml) were dissolved in dichloromethane (300 ml), and p-toluenesulfonic acid monohydrate (60 mg) was added to the solution, then the resulting mixture was heated under reflux for 12 hours. After cooling, triethylamine (0.14 ml) was added to the reaction mixture, and the resulting mixture was stirred for 15 minutes. Rough purification by flash column chromatography on silica gel (eluent: dichloromethane) and sequential purification by medium pressure liquid column chromatography on silica gel (eluent: hexane/diethyl ether=3/2) of the reaction mixture gave methyl 2-[2-benzyloxy-5-(2-methyl-1,3-dioxolan-2-yl) phenyl]acetate (9.2 g) as an oil.

IR (neat): 1742 cm$^{-1}$ $^1$H-NMR (CDCl$_3$) δ ppm: 1.65 (3H, s), 3.63 (3H, s), 3.68 (2H, s), 3.80–3.85 (2H, m), 4.00–4.05 (2H, m), 5.07 (2H, s), 6.88 (1H, d, J=8.4 Hz), 7.30–7.45 (7H, m)

Methyl 2-[2-benzyloxy-5-(2-methyl-1,3-dioxolan-2-yl)phenyl]acetate (9.0 g) was dissolved in diethyl ether (130 ml), and lithium aluminum hydride (1.0 g) was added portionwise to the solution under ice-cooling with stirring. After reaction for an hour, water was added portionwise to the reaction mixture under ice-cooling with stirring, and the resulting precipitates were filtered off. Concentration of the filtrate in vacuo gave 2-[2-benzyloxy-5-(2-methyl-1,3-dioxolan-2-yl)phenyl]ethanol (9.0 g) as an oil.

IR (neat): 3442 cm$^{-1}$ $^1$H-NMR (CDCl$_3$) δ ppm: 1.60–1.70 (4H, m), 2.96 (2H, t, J=6.5 Hz), 3.75–3.90 (4H, m), 3.95–4.10 (2H, m), 5.08 (2H, s), 6.89 (1H, dd, J=7.0, 2.0 Hz), 7.30–7.45 (7H, m)

2-[2-Benzyloxy-5-(2-methyl-1,3-dioxolan-2-yl)phenyl]ethanol (9.0 g) was dissolved in N,N-dimethylformamide (100 ml), and 60% sodium hydride in oil (1.26 g) was added to the solution under ice-cooling with stirring. After reaction for an hour at room temperature, benzyl bromide (3.75 ml) was added to the reaction mixture under ice-cooling with stirring, followed by reaction for 16 hours at room temperature. Ice (100 g) and water (100 ml) were added to the reaction mixture, and the resulting mixture was extracted with diethyl ether, then the solvent was removed in vacuo. The residue was dissolved in 1,2-dimethoxyethane (50 ml), and 1 N hydrochloric acid (10 ml) was added to the solution, then the resulting mixture was stirred for 30 minutes at room temperature. Water was added to the reaction mixture, and the resulting mixture was extracted with diethyl ether. The extract was dried over anhydrous magnesium sulfate, and the solvent was removed in vacuo. Purification of the residue by medium pressure liquid column chromatography on silica gel (eluent: hexane/diethyl ether=2/1) gave 4'-benzyloxy-3'-(2-benzyloxyethyl)acetophenone (8.5 g) as an oil.

IR (neat): 1677 cm$^{-1}$ $^1$H-NMR (CDCl$_3$) δ ppm: 2.54 (3H, s), 3.05 (2H, t, J=7.0 Hz), 3.73 (2H, t, J=7.0 Hz), 4.52 (2H, s), 5.13 (2H, s), 6.92 (1H, d, J=8.5 Hz), 7.20–7.40 (10H, m), 7.83 (1H, dd, J=8.5, 2.3 Hz), 7.86 (1H, d, J=2.3 Hz)

4'-Benzyloxy-3'-(2-benzyloxyethyl)acetophenone (8.0 g) and 30% hydrogen bromide acetic acid solution (0.4 ml) were dissolved in chloroform (80 ml), and a solution of bromine (1.1 ml) in chloroform (30 ml) was added dropwise to the solution over 2 hours at room temperature with stirring, then the resulting mixture was concentrated in vacuo. Purification of the residue by medium pressure liquid column chromatography on silica gel (eluent: hexane/diethyl ether=2/1) gave 4'-benzyloxy-3'-(2-benzyloxyethyl)-2-bromoacetophenone (3.9 g) having a melting point of 53–56° C.

IR (KBr): 1684 cm$^{-1}$ $^1$H-NMR (CDCl$_3$) δ ppm: 3.04 (2H, t, J=6.9 Hz), 3.73 (2H, t, J=6.9 Hz), 4.38 (2H, s), 4.51 (2H, s), 5.14 (2H, s), 6.95 (1H, d, J=8.4 Hz), 7.20–7.45 (10H, m), 7.85–7.90 (2H, m)

Water (20 ml) and dichloromethane (20 ml) were added to ethyl (S)-2-(2-amino-1,2,3,4-tetrahydronaphthalen-7-yloxy)acetate hydrochloride (600 mg), and sodium bicarbonate (300 mg) was added to the mixture under ice-cooling with stirring, then the resulting mixture was stirred for 30 minutes. The organic layer was separated and dried over anhydrous magnesium sulfate, then the solvent was removed in vacuo. The residue was dissolved in N,N-dimethylformamide (0.5 ml), and a solution of 4'-benzyloxy-3'-(2-benzyloxyethyl)-2-bromoacetophenone (440 mg) in N,N-dimethylformamide (1 ml) was added to the solution at −10° C. with stirring, followed by reaction for 20 minutes at 0° C. After cooling to −10° C. once again, sodium borohydride (190 mg) and ethanol (4 ml) were added to the reaction mixture with stirring. After reaction for 10 minutes at 0° C., the reaction mixture was poured into ice-water and extracted with ethyl acetate. The extract was washed with water and dried over anhydrous magnesium sulfate, then the solvent was removed in vacuo. The residue was dissolved in tetrahydrofuran (10 ml), and triethanolamine (0.7 ml) was added to the solution, then the resulting mixture was heated under reflux for 16 hours. After cooling, water was added to the reaction mixture, and the resulting mixture was extracted with ethyl acetate. The extract was washed with water and dried over anhydrous magnesium sulfate, then the solvent was removed in vacuo. Purification of the residue by medium pressure liquid column chromatography on silica gel (eluent: dichloromethane/ethanol=30/1) gave ethyl 2-[(2S)-2-[[(2RS)-2-[4-benzyloxy-3-(2-benzyloxyethyl)phenyl]-2-hydroxy ethyl]amino]-1,2,3,4-tetrahydronaphthalen-7-yloxy]acetate (540 mg) as an oil.

IR (neat): 3297, 1759, 1736 cm$^{-1}$ $^1$H-NMR (CDCl$_3$) δ ppm: 1.30 (3H, t, J=7.1 Hz), 1.50–1.65 (1H, m), 2.00–2.10 (1H, m), 2.50–2.85 (4H, m), 2.90–3.10 (5H, m), 3.72 (2H, t, J=7.3 Hz), 4.27 (2H, q, J=7.1Hz), 4.51 (2H, s), 4.57 (2H, s), 4.62 (1H, dd, J=9.0, 3.4 Hz), 5.06 (2H, s), 6.60 (1H, s), 6.69 (1H, dd, J=8.4, 2.7 Hz), 6.88 (1H, d, J=8.4 Hz), 6.99 (1H, d, J=8.4 Hz), 7.15–7.45 (12H, m)

EXAMPLE 1

Ethyl 5-[(2S)-2-[[(2RS)-2-hydroxy-2-(4-hydroxy-3-hydroxymethylphenyl)ethyl]amino]-1,2,3,4-tetrahydronaphthalen-7-yloxy]valerate (Compound 1)

Ethyl 5-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]valerate (207 mg) was dissolved in tetrahydrofuran (2 ml), and 1 N hydrochloric acid (2.0 ml) was added to the solution at room temperature. After reaction for an hour, the reaction mixture was concentrated in vacuo. A saturated aqueous sodium bicarbonate solution was added to the residue, and the resulting mixture was extracted with ethyl acetate. The extract was washed with brine and dried over anhydrous magnesium sulfate, and the solvent was removed in vacuo. Purification of the residue by medium pressure liquid column chromatography on aminopropyl silica gel (eluent: chloroform/methanol=10/1) gave ethyl 5-[(2S)-2-[[(2RS)-2-hydroxy-2-(4-hydroxy-3-hydroxymethylphenyl)ethyl]amino]-1,2,3,4-tetrahydronaphthalen-7-yloxy]valerate (Compound 1) (125 mg) as an amorphous.

IR (KBr): 3199, 1735 cm$^{-1}$ $^1$H-NMR (CDCl$_3$) δ ppm: 1.25 (3H, t, J=7.1 Hz), 1.55–1.65 (1H, m), 1.75–1.90 (4H, m), 2.00–2.10 (1H, m), 2.35–2.45 (2H, m), 2.50–3.05 (7H, m), 3.90–4.00 (2H, m), 4.13 (2H, q, J=7.1 Hz), 4.55–4.65 (1H, m), 4.82 (2H, s), 6.65–6.60 (1H, m), 6.67 (1H, dd, J=8.4, 2.6 Hz), 6.84 (1H, d, J=8.2 Hz), 6.98 (1H, d, J=8.4 Hz), 7.02 (1H, br s), 7.16 (1H, d, J=8.2 Hz)

EXAMPLE 2

Disodium 5-[(2S)-2-[[(2RS)-2-hydroxy-2-(3-hydroxymethyl-4-oxidophenyl)ethyl]amino]-1,2,3,4-tetrahydronaphthalen-7-yloxy]valerate (Compound 2)

Ethyl 5-[(2S)-2-[[(2RS)-2-hydroxy-2-(4-hydroxy-3-hydroxymethylphenyl)ethyl]amino]-1,2,3,4- tetrahydronaphthalen-7-yloxy]valerate (125 mg) was dissolved in ethanol (2 ml), and 2 N aqueous sodium hydroxide solution (274 μl) was added to the solution at room temperature with stirring. After reaction for 6 hours, concentration of the reaction mixture in vacuo gave disodium 5-[(2S)-2-[[(2RS)-2-hydroxy-2-(3-hydroxymethyl-4-oxidophenyl)ethyl]amino]-1,2,3,4-tetrahydronaphthalen-7-yloxy]valerate (Compound 2) (116 mg) as an amorphous.

IR (KBr): 3418, 1565 cm$^{-1}$ $^1$H-NMR (CDCl$_3$) δ ppm: 1.45–1.65 (1H, m), 1.70–1.80 (4H, m), 2.00–2.10 (1H, m), 2.15–2.30 (2H, m), 2.45–3.10 (7H, m), 3.85–4.00 (2H, m), 4.60–4.70 (3H, m), 6.55–6.70 (3H, m), 6.85–7.05 (2H, m), 7.10–7.20 (1H, m)

EXAMPLE 3

Ethyl 2-[(2S)-2-[[(2RS)-2-hydroxy-2-[4-hydroxy-3-(2-hydroxyethyl)phenyl]ethyl]amino]-1,2,3,4-tetrahydronaphthalen-7-yloxy]acetate (Compound 3)

Ethyl 2-[(2S)-2-[[(2RS)-2-[4-benzyloxy-3-(2-benzyloxyethyl)phenyl]-2-hydroxyethyl]amino]-1,2,3,4-tetrahydronaphthalen-7-yloxy]acetate (200 mg) and 10% palladium on activated carbon (30 mg) was suspended in acetic acid (1.5 ml), and the suspension was stirred for 6 hours at room temperature under a hydrogen atmosphere. The reaction mixture was filtrated to remove the catalyst, and the filtrate was concentrated in vacuo. Purification of the residue by medium pressure liquid column chromatography on aminopropyl silica gel (eluent: dichloromethane/ethanol= 10/1) gave ethyl 2-[(2S)-2-[[(2RS)-2-hydroxy-2-[4-hydroxy-3-(2-hydroxyethyl)phenyl]ethyl]amino]-1,2,3,4-tetrahydronaphthalen-7-yloxy]acetate (Compound 3) (120 mg) as an amorphous.

IR (KBr): 3293, 1752 cm$^{-1}$ $^1$H-NMR (CDCl$_3$) δ ppm: 1.27–1.32 (3H, m), 1.50–1.65 (1H, m), 2.00–2.10 (1H, m), 2.50–2.60 (1H, m), 2.65–3.05 (8H, m), 3.90–3.95 (2H, m), 4.27 (2H, q, J=7.1 Hz), 4.55–4.65 (3H, m), 6.55–6.60 (1H, m), 6.65–6.70 (1H, m), 6.86 (1H, d, J=8.2 Hz), 6.98 (1H, d, J=8.3 Hz), 7.05–7.15 (2H, m)

EXAMPLE 4

The following compounds were prepared according to a similar manner to that described in Example 1 using the corresponding ester compound instead of ethyl 5-[(2S)-2-[[(2RS)-2-(2,2-dimethylbenzo[1,2-d]-1,3-dioxan-6-yl)-2-hydroxyethyl]amino]-1,2,3,4-tetrahydronaphthalen-7-yloxy]valerate.

Ethyl 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate (Compound 4)

Amorphous

IR (KBr): 3191, 1763, 1752, 1738 cm$^{-1}$ $^1$H-NMR (DMSO-d$_6$) δ ppm: 1.15–1.25 (3H, m), 1.35–1.55 (1H, m), 1.70 (1H, br s), 1.85–2.00 (1H, m), 2.35–2.50 (1H, m), 2.55–3.00 (6H, m), 4.10–4.20 (2H, m), 4.40–4.55 (3H, m), 4.65–4.70 (2H, m), 4.94 (1H, br s), 5.08 (1H, br s), 6.55–6.70 (2H, m), 6.69 (1H, d, J=8.2 Hz), 6.95 (1H, d, J=8.2 Hz), 7.01 (1H, d, J=8.2 Hz), 7.25–7.30 (1H, m), 9.17 (1H, br s)

Ethyl 3-[(2S)-2-[[(2RS)-2-hydroxy-2-(4-hydroxy-3-hydroxymethylphenyl)ethyl]amino]-1,2,3,4-tetrahydronaphthalen-7-yl]acrylate (Compound 5)

Amorphous

IR (KBr): 3315, 1687, 1638 cm$^{-1}$ $^1$H-NMR (CDCl$_3$) δ ppm: 1.32 (3H, t, J=7.1 Hz), 1.55–1.75 (1H, m), 2.05–2.20 (1H, m), 2.60–3.15 (7H, m), 4.23 (2H, q, J=7.1 Hz), 4.30–5.20 (7H, m), 6.34 (1H, dd, J=16.0, 1.2 Hz), 6.76 (1H, d, J=8.1 Hz), 6.90–7.35 (5H, m), 7.57 (1H, d, J=16.0 Hz)

Ethyl 3-[(2S)-2-[[(2RS)-2-hydroxy-2-(4-hydroxy-3-hydroxymethylphenyl)ethyl]amino]-1,2,3,4-tetrahydronaphthalen-7-yl]propionate (Compound 6)

Amorphous

IR (KBr): 3184, 1733 cm$^{-1}$ $^1$H-NMR (CDCl$_3$) δ ppm: 1.24 (3H, t, J=7.1 Hz), 1.55–1.70 (1H, m), 2.00–2.15 (1H, m), 2.50–3.10 (11H, m), 4.13 (2H, q, J=7.1 Hz), 4.55–4.65 (1H, m), 4.82 (2H, s), 6.85 (1H, d, J=8.3 Hz), 6.89 (1H, br s), 6.90–7.10 (3H, m), 7.16 (1H, dd, J=8.3, 2.1 Hz)

Ethyl 5-[(2S)-2-[[(2RS)-2-hydroxy-2-(4-hydroxy-3-hydroxymethylphenyl)ethyl]amino]-1,2,3,4-tetrahydronaphthalen-7-yl]valerate (Compound 7)

Amorphous

IR (KBr): 3286, 1729 cm$^{-1}$ $^1$H-NMR (CDCl$_3$) δ ppm: 1.25 (3H, t, J=7.1 Hz), 1.50–1.75 (7H, m), 2.00–2.15 (1H, m), 2.31 (2H, t, J=7.0 Hz), 2.50–3.10 (9H, m), 4.12 (2H, q, J=7.1 Hz), 4.55–4.65 (1H, m), 4.85 (2H, s), 6.80–7.10 (5H, m), 7.18 (1H, dd, J=8.3, 2.1 Hz)

Ethyl 6-[(2S)-2-[[(2RS)-2-hydroxy-2-(4-hydroxy-3-hydroxymethylphenyl)ethyl]amino]-1,2,3,4-tetrahydronaphthalen-7-yl]hexanoate (Compound 8)

Amorphous

IR (KBr) : 3176, 1736 cm$^{-1}$ $^1$H-NMR (CDCl$_3$) δ ppm: 1.24 (3H, t, J=7.1 Hz), 1.30–1.45 (2H, m), 1.50–1.70 (5H, m), 2.00–2.10 (1H, m), 2.29 (2H, t, J=7.5 Hz), 2.50–3.10 (9H, m), 4.12 (2H, q, J=7.1 Hz), 4.55–4.65 (1H, m), 4.83 (2H, s), 6.80–7.10 (5H, m), 7.18 (1H, dd, J=8.3, 2.2 Hz)

EXAMPLE 5

The following compounds were prepared according to a similar manner to that described in Example 2 using the corresponding ester compound instead of ethyl 5-[(2S)-2-[[(2RS)-2-hydroxy-2-(4-hydroxy-3-hydroxymethylphenyl)-ethyl]amino]-1,2,3,4-tetrahydronaphthalen-7-yloxy]valerate.

Disodium 2-[(2S)-2-[[(2RS)-2-hydroxy-2-(3-hydroxymethyl-4-oxidophenyl)ethyl]amino]-1,2,3,4-tetrahydronaphthalen-7-yloxy]acetate (Compound 9)

Amorphous

IR (KBr): 3431, 1609 cm$^{-1}$ $^1$H-NMR (DMSO-d$_6$) δ ppm: 1.35–1.55 (1H, m), 1.80–2.00 (1H, m), 2.30–2.90 (8H, m), 3.95–4.10 (2H, m), 4.40–4.60 (3H, m), 5.00–5.20 (1H, m), 6.45–6.55 (2H, m), 6.65–6.75 (1H, m), 6.80–6.90 (1H, m), 6.95–7.05 (1H, m), 7.20–7.30 (1H, m)

Disodium 5-[(2S)-2-[[(2RS)-2-hydroxy-2-(3-hydroxymethyl-4-oxidophenyl)ethyl]amino]-1,2,3,4-tetrahydronaphthalen-7-yl]valerate (Compound 10)

Amorphous

IR (KBr): 3410, 1560 cm$^{-1}$ $^1$H-NMR (DMSO-$d_6$) δ ppm: 1.35–1.55 (6H, m), 1.80–2.00 (3H, m), 2.30–2.95 (10H, m), 4.20–4.30 (1H, m), 4.41 (2H, s), 4.56 (1H, br s), 5.93 (1H, d, J=8.2 Hz), 6.49 (1H, d, J=2.4 Hz), 6.62 (1H, dd, J=8.2, 2.4 Hz), 6.75–7.00 (3H, m)

Disodium 6-[(2S)-2-[[(2RS)-2-hydroxy-2-(3-hydroxymethyl-4-oxidophenyl)ethyl]amino]-1,2,3,4-tetrahydronaphthalen-7-yl]hexanoate (Compound 11)

Amorphous

IR (KBr): 3433, 1560 cm$^{-1}$ $^1$H-NMR (CD$_3$OD) δ ppm: 1.25–1.70 (7H, m), 1.95–2.20 (3H, m), 2.45–3.10 (9H, m), 4.60–4.70 (3H, m), 6.64 (1H, d, J=8.3 Hz), 6.80–7.10 (4H, m), 7.11 (1H, d, J=1.5 Hz)

EXAMPLE 6

6-[(2S)-2-[[(2RS)-2-Hydroxy-2-(4-hydroxy-3-hydroxymethylphenyl)ethyl]amino]-1,2,3,4-tetrahydronaphthalen-7-yl]hexanoic Acid (Compound 12)

Disodium 6-[(2S)-2-[[(2RS)-2-hydroxy-2-(3-hydroxymethyl-4-oxidophenyl)ethyl]amino]-1,2,3,4-tetrahydronaphthalen-7-yl]hexanoate (Compound 11) (20 mg) was dissolved in water (192 μl), and 1 N hydrochloric acid (77 μl) was added to the solution under ice-cooling with stirring. After reaction for 2 hours, the reaction mixture was concentrated in vacuo, and methanol was added to the residue. The insoluble material was filtered off, and the filtrate was concentrated in vacuo. Purification of the residue by medium pressure liquid column chromatography on octadecyl silica gel (eluent: water/acetonitrile=2/1) gave 6-[(2S)-2-[[(2RS)-2-hydroxy-2-(4-hydroxy-3-hydroxymethylphenyl)ethyl]amino]-1,2,3,4-tetrahydronaphthalen-7-yl]hexanoic acid (Compound 12) (12 mg) as an amorphous.

IR (KBr) : 3420, 1553 cm$^{-1}$ $^1$H-NMR (DMSO-$d_6$) δ ppm: 1.20–1.35 (2H, m), 1.40–1.60 (5H, m), 1.90–2.05 (1H, m), 2.18 (2H, t, J=7.2 Hz), 2.40–3.00 (9H, m), 4.47 (2H, s), 4.50–4.60 (1H, m), 5.00 (1H, br), 6.72 (1H, d, J=8.2 Hz), 6.85–7.00 (3H, m), 7.02 (1H, d, J=7.9 Hz), 7.29 (1H, s), 9.25 (1H, br)

TEST EXAMPLE 1

Action of Drugs on the Spontaneous Contractions of Isolated Pregnant Rat Myometrium The uteri of pregnant SD rats (pregnancy day 21) were isolated and longitudinal uterine muscle strips (about 15 mm in length and about 5 mm in width) free from the basal plate were prepared. The experiment was conducted according to the Magnus method. The sample with a tension of 1 g was exposed to Locke-Ringer solution maintained at 37° C. and gassed with a mixture of 95% of oxygen and 5% of carbon dioxide. The spontaneous contractions of the myometrium were induced isometrically via a pressure transducer and recorded on a rectigram. The drug efficacy was evaluated as 50% inhibitory drug concentration (i.e., EC$_{50}$ value) by comparing the total degree of uterine contraction during 5 minutes before the addition of the drug with the total degree of uterine contraction during 5 minutes after the addition of the drug.

TEST EXAMPLE 2

Action of Drugs on the Atrial Contractions of Isolated Atrium

The atria of SD male rats (350 to 400 g in body weight) were isolated and the experiment was conducted according to the Magnus method. The sample with a tension of 1 g was exposed to Krebs-Henseleit solution maintained at 37° C. and gassed with a mixture of 95% of oxygen and 5% of carbon dioxide. The atrial contraction was induced isometrically via a pressure transducer and recorded on a rectigram. After addition of the drug, its efficacy was evaluated as drug concentration that increased 20 beats per minute of heart rate (i.e., EC$_{20}$ value).

TEST EXAMPLE 3

Acute Toxicity Test

To 3 female ICR mice of 4 weeks age was administered intravenously ethyl 2-[(2S)-2-[[(2RS)-2-hydroxy-2-(4-hydroxy-3-hydroxymethylphenyl)ethyl]amino]-1,2,3,4-tetrahydronaphthalen-7-yloxy]acetate dissolved in saline at dose of 30 mg/kg. No death of animals was observed during 24 hours after the administration.

What is claimed is:

1. A 3,4-disubstituted phenylethanolaminotetralin-carboxylic acid derivative represented by the general formula:

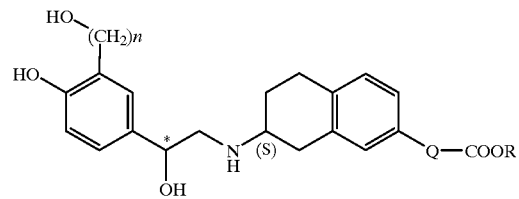

wherein Q represents a vinylene group or a group represented by the general formula:

-A-(CH$_2$)$_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration, or a pharmaceutically acceptable salt thereof.

2. A 3,4-disubstituted phenylethanolaminotetralin-carboxylic acid derivative as claimed in claim 1, represented by the general formula:

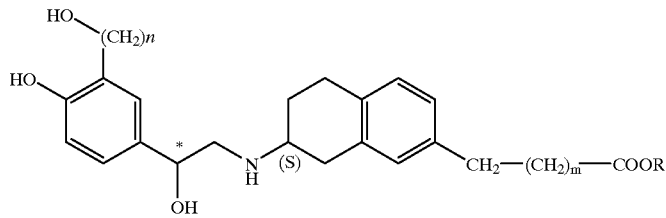

(wherein m is an integer of from 1 to 6; R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in s configuration) or a pharmaceutically acceptable salt thereof.

3. A pharmaceutical composition which comprises a 3,4-disubstituted phenylethanolaminotetralincarboxylic acid derivative represented by the general formula:

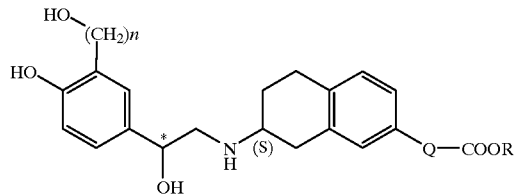

wherein Q represents a vinylene group or a group represented by the general formula:

-A-(CH$_2$)$_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration, or a pharmaceutically acceptable salt thereof.

4. A pharmaceutical composition as claimed in claim 3, which comprises a 3,4-disubstituted phenylethanolaminotetralincarboxylic acid derivative represented by the general formula:

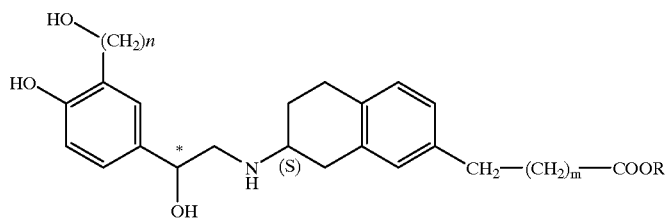

(wherein m is an integer of from 1 to 6; R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration) or a pharmaceutically acceptable salt thereof.

5. An agent for the prevention of threatened abortion and premature labor, a bronchodilator and an agent for pain remission and promoting stone removal in urolithiasis which comprises as the active ingredient a 3,4-disubstituted phenylethanolaminotetralincarboxylic acid derivative represented by the general formula:

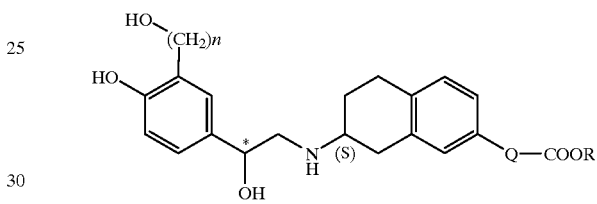

wherein Q represents a vinylene group or a group represented by the general formula:

-A-(CH$_2$)$_m$—

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration, or a pharmaceutically acceptable salt thereof.

6. An agent for the prevention of threatened abortion and premature labor, a bronchodilator and an agent for pain remission and promoting stone removal in urolithiasis as claimed in claim 5 which comprises as the active ingredient a 3,4-disubstituted phenylethanolaminotetralincarboxylic acid derivative represented by the general formula:

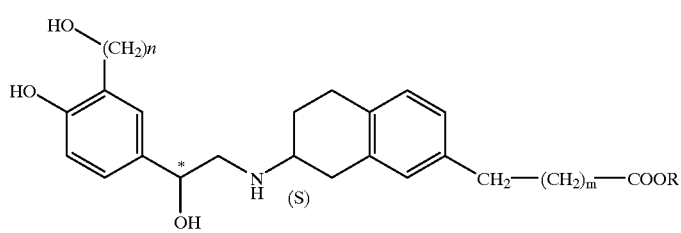

(Ia)

(wherein m is an integer of from 1 to 6; R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration) or a pharmaceutically acceptable salt thereof.

7. A method for prevention of threatened abortion and premature labor and the treatment of diseases associated with airway obstruction, which comprises administering a 3,4-disubstituted phenylethanolaminotetralincarboxylic acid derivative represented by the general formula:

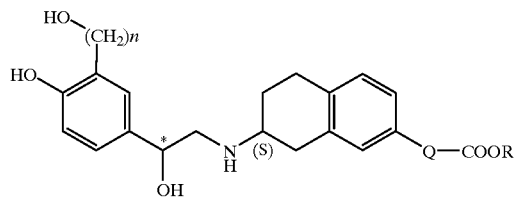

wherein Q represents a vinylene group or a group represented by the general formula:

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration, or a pharmaceutically acceptable salt thereof.

8. A method for pain remission and promoting stone removal in urolithiasis which comprises administering a 3,4-disubstituted phenylethanolamlnotetralincarboxylic acid derivative represented by the general formula:

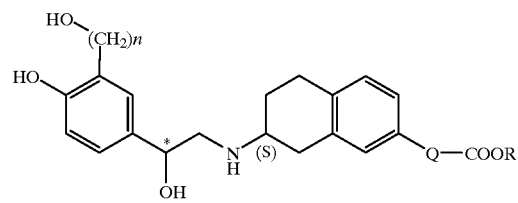

wherein Q represents a vinylene group or a group represented by the general formula:

(wherein A represents an oxygen atom or a methylene group; and m is an integer of from 1 to 6); R represents a hydrogen atom or a lower alkyl group; n is an integer of 1 or 2; the carbon atom marked with * represents a carbon atom in R configuration, S configuration or a mixture thereof; and the carbon atom marked with (S) represents a carbon atom in S configuration, or a pharmaceutically acceptable salt thereof.

* * * * *